(12) United States Patent
Lin et al.

(10) Patent No.: US 6,265,176 B1
(45) Date of Patent: Jul. 24, 2001

(54) DOT IMMUNOASSAY ON PLASTIC SHEETS

(75) Inventors: Tsue-Ming Lin; Seymour P. Halbert, both of Miami, FL (US)

(73) Assignee: Cordis Corporation, Miami, FL (US)

( * ) Notice: Subject to any disclaimer, the term of this patent is extended or adjusted under 35 U.S.C. 154(b) by 0 days.

(21) Appl. No.: 08/384,681

(22) Filed: Feb. 6, 1995

Related U.S. Application Data

(63) Continuation of application No. 08/020,481, filed on Feb. 18, 1993, now abandoned, which is a continuation of application No. 07/880,481, filed on May 6, 1992, now abandoned, which is a continuation of application No. 07/186,720, filed on Apr. 22, 1998, now abandoned, which is a continuation of application No. 06/792,431, filed on Oct. 29, 1985, now abandoned.

(51) Int. Cl.$^7$ .................................................. G01N 33/543

(52) U.S. Cl. ........................... 435/7.92; 435/5; 435/7.94; 435/7.95; 435/970; 435/975; 436/518; 436/531; 436/809; 422/56; 422/57; 427/2; 427/2.11

(58) Field of Search ............................ 435/5, 7.92, 7.94, 435/7.95, 970, 975; 436/531, 809, 518; 422/57, 56; 427/2.11, 2

(56) References Cited

U.S. PATENT DOCUMENTS

| | | | |
|---|---|---|---|
| 4,376,110 | 3/1983 | David et al. | 436/513 |
| 4,474,878 | * 10/1984 | Halbert et al. | 435/7 |
| 4,496,654 | 1/1985 | Katz et al. | 435/7 |
| 4,594,225 | * 6/1986 | Arai et al. | 422/56 |
| 5,126,276 | * 6/1992 | Fish et al. | 436/531 |

FOREIGN PATENT DOCUMENTS

| | | | |
|---|---|---|---|
| 0063810 | * 11/1982 | (EP) | 435/7.92 |
| 0125118 | * 11/1984 | (EP) | 435/7.92 |
| 0130434 | * 1/1985 | (EP) | 436/531 |

OTHER PUBLICATIONS

H. Towbin et al, "Immunoblotting and Dot Immunobinding—Current Status and Outlook," *J. of Immunol. Methods* 72(2):313–340, 1984.*

Shamberger, R., "Elisa on the Trail of Viral Diseases," *Diagnostic Medicine*, Oct. 1984, pp 52–57.*

Pappas et al "Dot Enzyme–Linked Immunosorbent Assay (Dot–Elisa): a MicroTechnique for the Rapid Diagnosis of Visceral Leishmaniasis," *J. of Immun Meth*, 64 (1983) 205–214.*

Grant & Hackh's *Chemical Dictionary*, Fifth Edition, (McGraw–Hill Book Company New York), 1987, p. 3.*

Pappas et al, *Journal of Immunological Methods*, 64 (1983) 205–214.*

Shamberger, R., *Diagnostic Medicine*, Oct. 1984, pp 52–57.*

Lin et al, "Rapid Dot Enzyme Immunoassay for the Detection of Antibodies to Cytomegalovirus", *J. Clin. Micro.*, V.24, No. 1, pp. 7–11.*

Carlson et al, "Rapid Easy and Economical Screening Test for Antibodies to Human Immunodeficiency Virus", *Lancet*, Feb 14, 1987, pp. 361–362.*

(List continued on next page.)

Primary Examiner—Bao-Thuy L. Nguyen
(74) Attorney, Agent, or Firm—Fish & Richardson PC

(57) ABSTRACT

Analytical test kits and assay procedure employs test cards or strips of an inert plastic carrier having a flat, non-absorbent surface, containing thereon spots of insolubilized reagent for the determination of an analyte, such as an antigen or an antibody, in a liquid medium such as serum or other body fluids in a solid phase enzyme immunoassay of the sandwich type. Different binding partners can be placed as separate spots on the same card for the assay of a group of related or unrelated analytes in the same test sample. An insoluble colored product on a spot, qualitatively and quantitatively, is indicative of a positive result.

35 Claims, 1 Drawing Sheet

OTHER PUBLICATIONS

Hawkes et al., "A Dot–Immunobinding Assay for Monoclonal and Other Antibodies," *Anal. Chem.* 119: 142–147 (1982).

Renart, "Transfer of Proteins form Gels to Diazobenzyloxymethylpaper and Detection with Antisera: A Method for Studying Antibody Specificity and Antigen Structure," *Proc. Nat'l Acad. Sci. USA*, 76.7, 3116–20 (Jul. 1979).

Towbin et al., "Electrophoretic Transfer of Proteins from Polyacrilamide Gels to Nitrocellulose Sheets: Procedures and Same Application," *Proc. Natl. Acad. Sci. USA*, 76.9, 4350–54 (Sep. 1979).

Towbin and Gordon, "Immunoblotting and Dot Immunobinding—Current Status and Outlook," J. Immuno. Methods, 72: 313–40 (1984).

Pappas et al., "Dot Enzyme–Linked Immunosorbent Assay (Dot–Elisa): a Micro Technique for the Rapid Diagnosis of Visceral Leishmaniasis," *Journal of Immunological Methods* 64: 205–214 (1983).

\* cited by examiner

DOT IMMUNOASSAY ON PLASTIC SHEETS

This application is a continuation of Ser. No. 08/020,481, filed Feb. 18, 1993, now abandoned, which is a continuation of Ser. No. 07/880,481 filed May 6, 1992, now abandoned, which is a continuation of Ser. No. 07/186,720 filed Apr. 22, 1988, now abandoned, which is a continuation of Ser. No. 06/792,431 filed Oct. 29, 1985, now abandoned.

BACKGROUND OF THE INVENTION

This invention relates to the detection of components of the antigen-antibody reaction by solid phase immunoassay techniques, more particularly to enzyme immunoassay.

Many immunoassay procedures for detecting antigens, antibodies and haptens in body fluids are known in the immunoassay art. Radio-immunoassay techniques are numerous and have been shown to be highly sensitive. Numerous enzyme-immunoassay techniques are also known, including competitive, double antibody solid phase ("DASP") and sandwich procedures. Both classes of solid phase immunoassays have been performed using various solid supports, including finely divided cellulose, solid beads or discs, polystyrene tubes and microtiter plates.

Enzyme immunoassays have included color formation as an indicator of a result. Degree of color formation has been used for quantitative determinations. Colorimeters have been used for automatic quantitative determinations based on color gradations of analytical solutions.

Dot enzyme-linked immunosorbent assays using nitrocellulose filters as the solid phase have recently been described by Hawkes et al., "A Dot-Immunobinding Assay for Monoclonal and Other Antibodies," Anal. Biochem. 119, 142–147 (1982). Hawkes et al. described putting antigen spots on nitrocellulose filters, cutting out areas containing spots, and either placing the cut-out portions in the wells of microtiter plates for enzyme immunoassasy or, where a range of different antigens are to be screened, using nitrocellulose strips. Similarly, Pappas et al., "Dot Enzyme-Linked Immunosorbent Assay (Dot-ELISA): a Micro Technique for the Rapid Diagnosis of Visceral Leishmaniasis," J. Imm. Meth. 64, 205–214 (1983), have disclosed a dot assay for parasites. Both Hawkes et al. and Pappas et al. asserted advantages of nitrocellulose dot (or spot) assays, including not only a reduced need for bound reagent, but also the almost-whiteness of nitrocellulose as a background for color reading. Pappas et al. also stressed the improved binding of bound reagent to nitrocellulose as compared to microtiter plate wells. Hawkes et al. disclosed a quantitative procedure in which reflectance of spots was determined by a thin layer scanner.

Also known in the art are pregnancy tests which utilize dipsticks coated or partially coated with bound antibody to HCG, such as the PREGNASTICK pregnancy test kit sold by Monoclonal Antibodies, Inc. Enzyme immunoassay procedures are used to change the color of the coated portion of the dipstick.

The myriad assays in the prior art, while providing in some instances very high sensitivity, suffer from a variety of drawbacks. Radio-immunoassay procedures require the handling of radioactive materials, as well as their disposal, and expensive equipment. Many enzyme-immunoassay procedures produce soluble color solutions, are used with colorimeters, and require incubation periods longer than desired. Enzyme immunoassay pregnancy tests utilize single-use kits, which are thrown away after a single use. The nitrocellulose-based dot tests utilize a solid support which may absorb reactants, which can lead to background color and reduced sensitivity. Further, nitrocellulose is fragile, making it difficult to handle.

It is a principal object of this invention to provide an improved immunoassay kit and protocol which eliminates drawbacks, discussed above, of the prior art and is capable of achieving an immunoassay which is sensitive, fast, inexpensive, which does not require expensive and delicate instruments, which is usable for multiple assays, and which can be made for a qualitative or a quantitative test. This and other objects of this invention will be better understood by reference to the description which follows.

SUMMARY OF THE INVENTION

We have developed a new dot test for assaying body fluids for components (antigens, antibodies, haptens) of the antigen-antibody reaction employing an enzyme-immunoassay technique, and a kit of reagents for carrying out multiple assays. The kit includes a white opaque plastic card having identifiable small spots or dots containing thereon insolubilized binding partner of the component to be determined. The plastic card contains a preselected number of spots and may be cut into strips so that one may use only the necessary number of spots, saving the remainder for other assays. Other reagents include an enzyme conjugate, comprising a color-promoting enzyme bound to a binding partner of the component to be determined; a substrate capable of reacting with the bound enzyme to produce an insoluble colored product; and preferably control samples, specimen diluent and wash solution. The kit may include all necessary laboratory ware to perform assays. Assay instructions are included in the kit.

The spots on the card may all be one insolubilized reagent or they may be more than one reagent for testing for multiple unknowns. The latter case is particularly suited for assaying for antibodies. In that event the enzyme conjugate comprises an enzyme bound to an antibody to the class of antibodies being sought, such as, for example anti-human IgG, so that only one conjugate is required for the entire series of tests.

In the assay procedure, a small drop of body fluid which may contain the component to be determined is placed on a spot on the card containing insolubilized binding partner of that component. After a short incubation at room temperature, the spot is preferably washed and blotted dry. Next a small drop of enzyme conjugate capable of binding to the component to be determined is added to the spot. Following a short incubation at room temperature, the spot is washed to remove unbound conjugate and blotted dry. Next, a small drop of substrate is added to the spot. The substrate comprises a material which reacts with the enzyme to produce in a short time and at room temperature an insoluble colored product. The intensity of the color is proportional to the sample's concentration of component to be determined and can easily be read by the naked eye without the aid of instrumentation. No color is developed if the test sample contains none of the component to be determined.

The invention includes a process for the rapid and simple determination of the presence in a test sample of body fluid of a component to be determined of the antigen-antibody reaction, comprising:

a. applying a drop comprising concentrated test sample diluted 1:10 or less to an identifiable spot of about 1 cm diameter on a flat, opaque, inert plastic carrier, said spot comprising insolubilized first binding partner of the component to be determined;

b. incubating at room temperature for up to one-half hour;
c. removing unbound body fluid;
d. applying a drop of concentrate conjugate comprising an enzyme coupled to a second binding partner of the component to be determined;
e. incubating at room temperature for up to one-half hour;
f. washing;
g. applying a drop of enzyme substrate comprising a material capable of reacting with the enzyme at room temperature to form in a few minutes a colored deposit readable by the naked eye against the background of the opaque plastic carrier.

BRIEF DESCRIPTION OF THE DRAWINGS

In the accompanying drawing, FIG. 1, there is depicted in plan view a plastic card having identifiable spots of insolubilized binding partner, according to this invention.

DETAILED DESCRIPTION OF THE INVENTION

Figure 1:
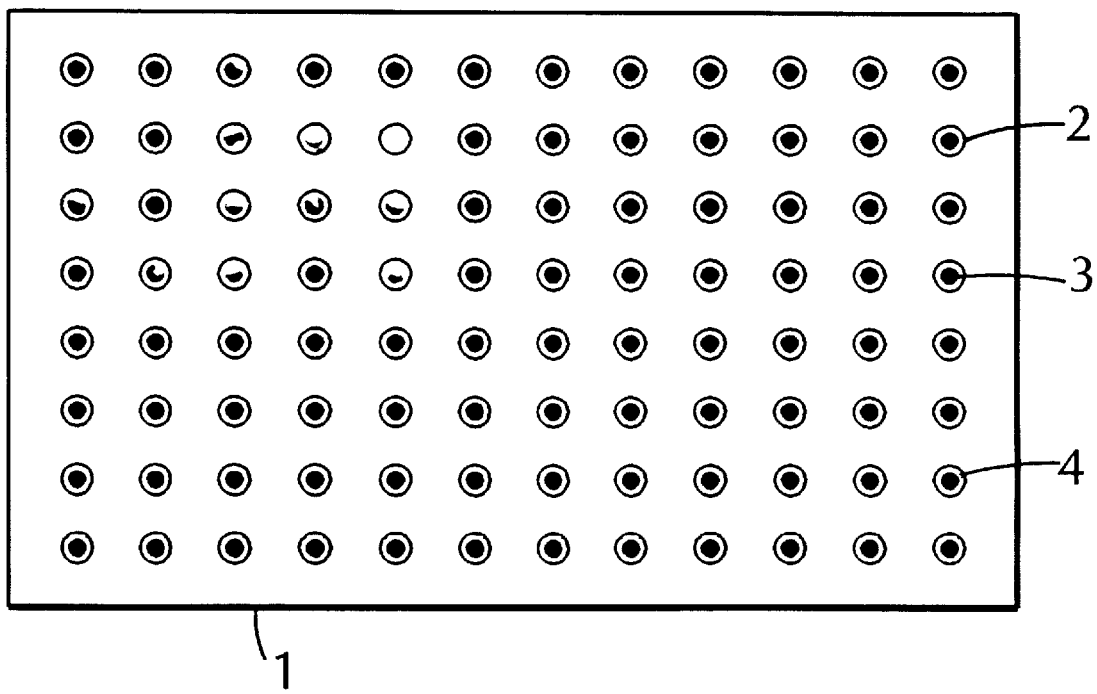

The solid phase assay of this invention utilizes as a solid carrier a plastic sheet or card having on it surface spots containing insolubilized binding partner of the component to be determined. The card should be opaque. Most preferably it is white, to provide excellent background against which to determine color formation in the active spots or dots. The card should have sufficient thickness to impart opacity, to reduce fragility, and to provide ease of handling. Beyond that, the card may be of any thickness.

The card may be made of opaque plastic to which the insolubilized binding partner or binding partners will adhere, so long as the card material does not itself adversely affect the assay to be performed. Suitability of a given plastic material can be determined easily by simply trying the material for the desired assay. We have found opaque, white high impact polystyrene to be the most preferred card material. It provides a superior background for determining color formation as compared to nitrocellulose. High impact polystyrene is marketed as sheets having one glossy side and one matte-finish side. We use the matte-finish side for our preferred reagent. A polyethylene which we tested, on the other hand, was found to give unsatisfactory results for the particular assay in which it was tested. High impact polystyrene is hydrophobic, and it is possible that there may be some ionic bonding between the plastic and the insolubilized reagent, but the manner of bonding is not known with certainty.

Referring to the preferred embodiment shown in FIG. 1, 1 is a sheet or card of white, opaque high impact polystyrene. Spot identifiers 2 are outlined circles slightly less than 1 cm. in diameter. Card 1 contains twelve columns each of eight rows of spot identifiers 2, spaced approximately 1 cm. apart. A description of the reagents of the kit and of the assay procedure will now be given with respect to an assay of human serum for antibodies against cytomegalovirus ("CMV") antigen. It will be understood that this invention is not limited to antibodies against CMV antigen as the component to be determined and that the invention includes generally components of the antigen-antibody reaction.

Preparation of the Insolubilized Reagent

Binding partner of the component to be determined is insolubilized as spots on the plastic carrier sheet or card. Four microliters of cytomegalovirus antigen solution are placed in the form of drops onto all of the spot identifiers 2 of card 1. That procedure may be repeated as necessary to form spots 3 of 1–4 mm. in diameter in all of the spot identifiers 2. We prefer to aim for spots of 2 mm. in diameter. This leaves an uncoated annulus 4, which serves as a form of negative control, when unknown and test reagents are added to the entire circle. The cards are incubated overnight in a humid box at 4° C. and then dried in an oven at 53° C. for 5–15 minutes.

For storage prior to use the card is stored with a dessicant at 4° C. The card can be thus stored for extended periods. Storage of cards containing CMV antigen at room temperature, on the other hand, has been found to lead to a minor diminution in sensitivity after three months.

It may be desirable to prepare the insolubilized reagent as a card having multiple rows and columns of spots, as in FIG. 1 but to store the card in another form, such as narrow strips. We have cut cards into strips for storage in a test tube to which dessicant is added.

Test Kit of Reagents

A test kit according to this invention includes cards or strips containing insolubilized binding partner, whose preparation is described above, plus additional reagents. These include in all cases conjugate comprising enzyme coupled to a binding partner of the component to be determined. This binding partner may be the same as the insolubilized binding partner but it need not be, as will be described below. Preparation of enzyme conjugates is well known in the art and will not be discussed here. Also, a test kit will in all cases include an enzyme substrate capable of forming an insoluble colored product when reacted with the enzyme of the conjugate. We have found that 5-bromo-4-chloro-3-indolyl phosphate, which is colorless but reacts with alkaline phosphatase to form an insoluble blue product, is particularly well suited for this invention.

The test kit preferably also includes a washing solution. We have found tris-saline with 0.05% TWEEN 20 surfactant to be a preferred washing solution.

The kit may include an inert specimen diluent. The kit may also include a control serum to show a negative result or a control serum to show a positive result or, most preferably, both.

A test kit according to this invention may include a carrier comprising a card having printed thereon circular identifiers about 1 cm in diameter or a carrier comprising strips having printed thereon circular identifiers about 1 cm in diameter.

Where the kit is designed for home or field use, the kit may also include the simple laboratory ware for performing the assay, pipets and blotting papers, for example.

Conduct of the Assay

Test kit reagents and materials, and test serum samples are first brought to room temperature. Normally about 15 minutes is adequate for this purpose.

In the assay for CMV antibodies described here in detail serum samples, both test and controls, are diluted 1:10 with specimen diluent. We note that undiluted sera can be tested, in which case incubation times may be reduced somewhat. Incubation of undiluted serum with the insolubilized CMV can be as short as 5 minutes, for example.

The undiluted and diluted sera used for the assay of this invention are more concentrated than for the standard CORDIA test, a commercial ELISA test, which employs dilutions of 1:50 or 1:100. The difference in concentration ranges from a factor of five to as large as a factor of 100.

One drop (20–25 microliters) of diluted test serum is added to one spot 3 of a circle 2 on a strip from card 1. A drop of diluted negative control serum is added to a spot of another circle. A drop of diluted positive control serum is added to a spot of yet a third circle. The spots, as described above, already contain insolubilized CMV antigen. The card (strip) is allowed to incubate at room temperature for 20 minutes, following which the unbound portion of test serum and the control sera are removed by rinsing or by means of a pipet.

The card (strip) is washed twice for 5 minutes each time by dipping it into a test tube of the wash solution, tris-saline with 0.05% TWEEN 20 surfactant. The strip is blotted dry with bibulous papers.

To the dried card (strip) a small drop of conjugate of appropriate concentration is added. The conjugate for the assay of this invention is highly concentrated; that is, an order of magnitude or more, preferably about twenty to thirty times more, than the concentration of conjugate used in ELISA tests such as the commercial CORDIA test. The conjugate we use for this CMV antibody assay is alkaline phosphatase coupled to antibody to human immunoglobulin. We use it in a concentration of 50 micrograms per ml.

By (1) testing for antibodies rather than antigens, and (2) using antibody to human immunoglobulin for the conjugate preparation, one conjugate can be used for assaying for a series of antibodies such as, for example, TORCH antibodies (to *Toxoplasma gondii,* rubella, CMV and *Herpes simplex,* four infections causing prenatal problems in pregnancy). This permits a simpler and more error-free assay procedure and a simpler and more inexpensive kit.

The strip is then permitted to incubate at room temperature, washed twice as above and dried with bibulous paper. For a particular assay the incubation time can be predetermined as the amount of time up to thirty minutes after which there is little or no final color change with additional incubation. For our CMV antibody test described herein, we have reduced the incubation time to 5 min.

Finally, one small drop of substrate is added to each test and control spot. The substrate we use for the CMV antibody test is 5-bromo-4-chloro-3indolyl phosphate (5B4C3I) (2 mg/ml). It is a colorless substrate which reacts with alkaline phosphatase by splitting off phosphate and producing a blue deposit. Other suitable color-forming substrates will be apparent to persons skilled in the art. The spots are observed for the first 5 minutes and after 20 minutes. Absence of color after 20 minutes indicates a negative result. The color developed within the first few minutes is proportional to the concentration of CMV antibody in the test serum and can be read easily by the naked eye.

Although described above for a qualitative assay, a quantitative determination can be made by preparing serial dilutions of positive samples and retesting to see if a positive result is obtained at increasing dilutions. Reflective photometry is expected to assist in quantifying the amount of color obtained from test samples.

Record of Test Results

The card (strip) on which an assay was performed is small and thin. It can be rinsed with water, shaken dry, and kept as a convenient record in a patient file or experimental notebook. No separate storage device is required. Strips have been stored for about a year without apparent diminution of the blue color from positive tests.

Test Sensitivity

Surprisingly, we have found that the sensitivity of the assay of this invention, which utilizes only about 200 ng. of antigen per spot, approximately equals the sensitivity of the CORDIA ELISA test, which utilizes about 5000 ng. per one-cm. disc. It is not understood why this level of sensitivity is achieved, although we speculate that the high concentrations of reactants may be responsible, at least in part.

We claim:

1. A test kit for detecting the presence in a sample of at least one component to be detected selected from the group consisting of antigens, antibodies and hastens by a sandwich enzyme immunoassay comprising in one or more containers:

a. an analytical device consisting essentially of an inert, opaque plastic carrier having a flat, hydrophobic surface that is non-absorbent to said antigens, antibodies, hastens and to enzymes, having a multiplicity of visually locatable discrete locations and, deposited directly on said surface within at least one of said discrete locations, a spot of an insolubilized specific first binding partner of the at least one component to be detected;

b. a working reagent conjugate of predetermined concentration of at least about 15 micrograms per ml in liquid form comprising an enzyme coupled to a specific second binding partner of the at least one component to be detected; and c. an enzyme substrate in liquid form comprising a material capable of reacting with said enzyme at room temperature to form a colored precipitate detectable by the naked eye against said opaque carrier.

2. The test kit according to claim 1 wherein said sample is a human body fluid, wherein the at least one component to be detected comprises at least a first human antibody and a second human antibody, wherein at least one of said discrete locations contains a spot of insolubilized, specific first binding partner of said first human antibody and at least another of said discrete locations contains a spot of insolubilized specific first binding partner of said second human antibody, and wherein said conjugate comprises an enzyme coupled to an antibody to human immunoglobulin.

3. The test kit according to claim 2 wherein said at least one component to be detected selected from the group consisting of antibodies to *Toxoplasma gondii,* rubella, cytomegalovirus, and *Herpes simplex.*

4. The test kit according to claim 2 wherein said carrier is a polystyrene plastic.

5. The test kit according to claim 1 wherein said carrier is a polystyrene plastic.

6. The test kit according to claim 5 wherein said carrier is white, high-impact polystyrene.

7. The test kit according to claim 1, wherein said carrier comprises at least two of said discrete locations, wherein at least two of said discrete locations contain a spot of said insolubilized, specific first binding partner of the at least one component to be detected, and wherein said test kit includes a positive control fluid.

8. The test kit according to claim 7, wherein said carrier comprises at least three discrete locations, wherein said at least three of said discrete locations contain a spot of said insolubilized, specific first binding partner of the at least one component to be detected, and wherein said test kit includes a negative control fluid.

9. The test kit according to claim 7 further comprising a wash solution.

10. The test kit according to claim 1 wherein said visually locatable, discrete locations are each outlined by a circle about 1 cm in diameter.

11. The test kit according to claim 10 wherein said spots are from 1 to 4 mm in diameter.

12. The test kit according to claim 11 wherein said carrier is a polystyrene plastic.

13. The test kit according to claim 10 wherein said carrier comprises a card and said circles are about 1 cm apart.

14. The test kit according to claim 10 wherein said carrier comprises a strip and said circles are about 1 cm apart.

15. The test kit according to claim 1, wherein said surface has a matte finish.

16. The test kit according to claim 1, wherein said specific second binding partner is an antiimmunoglobulin antibody.

17. The test kit according to claim 1 wherein said specific second binding partner is an antigen.

18. A sandwich enzyme-immunoassay test kit for detecting the presence in a sample of at least one component of an antigen-antibody reaction comprising:
   a. flat, inert, opaque non-absorbent, hydrophobic plastic carrier means having thereon a plurality of spaced apart, outlined circles about 1 cm in diameter, within at least one of which is a spot, from 1 to 4 mm in diameter, of insolubilized, specific first binding partner for said at least one component, deposited directly on said plastic carrier means;
   b. a first working fluid comprising at least 15 micrograms per ml of a conjugate of an enzyme coupled to a specific second binding partner for of said at least one component; and
   c. a second fluid comprising a substrate reactable with said enzyme to form a colored precipitate.

19. The test kit according to claim 18 for detecting the presence of a plurality of human antibodies, wherein at least one of said circles contains a spot of insolubilized antigen specific for one of each of said plurality of antibodies, and wherein said conjugate comprises an enzyme coupled to antibody to human immunoglobulin.

20. A sandwich enzyme-immunoassay process for detecting the presence in a sample from the group consisting of body fluid and the body fluid diluted 1:10 or less of at least one component to be detected selected from the group consisting of antigens, antibodies and haptens, comprising:
   a. applying a drop of said sample onto one of a plurality of visually locatable, discrete locations on a flat, hydrophobic surface, that is non-absorbent to said antigens, antibodies and haptens and to enzymes, of an inert, opaque plastic carrier, said location having deposited directly thereon a spot of insolubilized specific, first binding partner of the at least one component to be detected;
   b. incubating said carrier for up to one-half hour to immobilize said at least one component to be detected;
   c. removing unbound body fluid;
   d. applying onto each of said discrete locations a drop of first fluid comprising at least 15 micrograms per ml of a conjugate of an enzyme coupled to a specific second binding partner of the component to be detected;
   e. incubating at room temperature for up to one-half hour to immobilize said conjugate;
   f. washing away unbound conjugate;
   g. applying onto said discrete location a drop of a second fluid comprising a substrate reactable with said enzyme at room temperature to form within about five minutes a colored precipitate visually detectable against said opaque carrier; and
   h. visually ascertaining the presence or absence of the colored precipitate as indicative of the presence or absence of said at least one component to be detected.

21. The process of claim 20, wherein the substrate is visually detectable to the naked eye, and the step of visually ascertaining is ascertaining by the naked eye.

22. The process of claim 20 further comprising a washing step before applying the drop of conjugate.

23. The process of claim 20, wherein said carrier comprises at least two discrete locations, wherein a second of the plurality of discrete locations has deposited directly thereon a spot of the specific, first binding partner of the at least one component to be detected, and steps "a" through "g" are repeated at said second location with a positive control fluid.

24. The process of claim 23, wherein said carrier comprises at least three discrete locations, wherein a third of the plurality of discrete locations has deposited directly thereon a spot of the specific, first binding partner of the at least one component to be detected, and steps "a" through 'G' are repeated at said third location with a negative control fluid.

25. The process of claim 20, wherein the body fluid is diluted up to 1:10 before being applied to said one of a plurality of discrete locations.

26. The process of claim 20 for detecting at least a first antibody and a second antibody in human body fluid, wherein said one location has deposited thereon a spot of specific, first binding partner of said first antibody, wherein a second location has deposited thereon a spot of specific, first binding partner of said second antibody, wherein said specific second binding partner is antibody to human immunoglobulin, and wherein steps "a" through "g" are performed at both locations.

27. The process of claim 20, wherein said surface has a matte finish.

28. The process of claim 20, wherein said specific second binding partner is an antiimmunoglobin antibody.

29. The process according to claim 20 wherein said specific second binding partner is an antigen.

30. An analytical device for use in a sandwich enzyme immunoassay for detecting the presence in a body fluid of at least one component to be detected selected from the group consisting of antigens, antibodies and hastens, consisting essentially of an inert, opaque plastic carrier having a flat, hydrophobic surface that is non-absorbent to said antibodies, antigens and hastens and to enzymes having deposited directly thereon an insolubilized specific binding partner of the at least one component to be detected in the form of spots of from 1 to 4 mm in diameter in discrete, visually locatable locations.

31. The device according to claim 30 wherein said surface has deposited thereon a first insolubilized specific binding partner of a first component to be detected in at least one of said discrete locations and a second insolubilized specific binding partner of a second component to be detected in at least another of said discrete locations.

32. The device according to claim 30, wherein said carrier is a polystyrene.

33. The device according to claim 32, wherein said carrier is high-impact polystyrene.

34. The device according to claim 30, wherein said visually locatable, discrete locations are each outlined by a circle about 1 cm in diameter and are larger than said spots.

35. The device according to claim 30, wherein said surface has a matte finish.

* * * * *